United States Patent [19]
Van Wezel, deceased et al.

[11] Patent Number: 4,888,294
[45] Date of Patent: Dec. 19, 1989

[54] APPARATUS AND METHOD FOR THE CONTINUOUS CULTIVATION OF MICROORGANISMS IN A CULTURE LIQUID

[75] Inventors: Antonius L. Van Wezel, deceased, late of Bilthoven, Netherlands, by Cornelia Maria Berendse; Hans H. De Haan, Bilthoven; Stephan Vermeij, Nieuwegein, both of Netherlands

[73] Assignee: Nederlanden Vertegenwoordigd, Leidschendam, Netherlands

[21] Appl. No.: 262,237

[22] Filed: Oct. 21, 1988

Related U.S. Application Data

[63] Continuation of Ser. No. 934,110, Nov. 24, 1986, abandoned.

[30] Foreign Application Priority Data

Nov. 25, 1985 [NL] Netherlands ........................ 8503245

[51] Int. Cl.$^4$ .............................................. C12M 1/02
[52] U.S. Cl. ..................................... 435/316; 435/286
[58] Field of Search ........ 435/284, 286, 287, 311–316; 210/208, 213, 218, 219, 220, 297, 298, 314, 326, 342, 515

[56] References Cited

U.S. PATENT DOCUMENTS

| | | | |
|---|---|---|---|
| 2,491,801 | 12/1949 | Debrey | 210/57 |
| 2,651,416 | 9/1953 | Van der Mark et al. | 210/297 |
| 2,767,847 | 10/1956 | Russell et al. | 210/208 |
| 3,168,431 | 2/1965 | Spielvogel | 435/316 |
| 3,400,051 | 9/1968 | Hofschneider | 435/316 |
| 3,437,208 | 4/1969 | Kaspar et al. | 210/297 |
| 3,528,889 | 9/1970 | Porto | |
| 3,599,792 | 8/1971 | Swipp | 210/297 |
| 3,647,632 | 3/1972 | Johnson et al. | 435/311 |
| 3,651,945 | 3/1972 | Feren | 210/324 |
| 4,040,965 | 8/1977 | Kohlheb | 210/297 |
| 4,166,768 | 9/1979 | Tolbert et al. | 435/286 |
| 4,263,143 | 4/1981 | Ebner et al. | 435/315 |
| 4,310,630 | 1/1982 | Girard et al. | 435/284 |
| 4,328,317 | 5/1982 | Prentice et al. | 435/316 |
| 4,342,835 | 8/1982 | Hitzman et al. | 435/315 |
| 4,380,584 | 4/1983 | Hitzman | 435/316 |
| 4,535,062 | 8/1985 | Muller | 435/312 |
| 4,634,675 | 1/1987 | Freedman et al. | 435/316 |

FOREIGN PATENT DOCUMENTS

| | | |
|---|---|---|
| 697045 | 4/1967 | Belgium . |
| 723611 | 5/1969 | Belgium . |
| 0191356 | 2/1986 | European Pat. Off. ............ 435/286 |
| 1808243 | 6/1969 | Fed. Rep. of Germany . |
| 1642584 | 7/1971 | Fed. Rep. of Germany . |
| 3229748 | 2/1983 | Fed. Rep. of Germany . |
| 1534731 | 6/1968 | France . |
| 1591000 | 4/1970 | France . |
| 2511031 | 11/1983 | France . |
| 58-098083 | 6/1983 | Japan . |
| 6705311 | 10/1967 | Netherlands . |
| 6715384 | 5/1969 | Netherlands . |
| 137389 | 4/1973 | Netherlands . |
| 8204606 | 8/1982 | Sweden . |
| 1165328 | 9/1969 | United Kingdom . |
| 1190516 | 5/1970 | United Kingdom . |
| 1356794 | 6/1974 | United Kingdom . |
| 2106540 | 4/1983 | United Kingdom . |

OTHER PUBLICATIONS

Use of a Rotating Wire Cage for Retention of Animal Cells in a Perfusion Fermentor, R. Varecka and W. Scheirer, Develop. Biol. Standard., vol. 66, pp. 269–272, 5-1987.

Primary Examiner—Noah P. Kamen
Attorney, Agent, or Firm—Brumbaugh, Graves, Donohue & Raymond

[57] ABSTRACT

Cultivation tank (1) for continuous cultivation of cells or micro-organisms, containing a rotating separating device (11,12) for separating suspended cells from cultivation liquid (10) supplied continuously through a supply (4) and passed through the separating device (11,12) from the outside to the inside, cell free liquid being continuously discharged from within the separating device (11,12), the rotating parts (11,12) of the separating device being formed so that within the outer circumference a zone (15) is formed of a vortex-free, vertical rotating column of cultivation liquid from which the cells are radially thrown out by centrifugal forces into the surrounding liquid (10) through openings in the outlet circumference (11) of the separating device (11,12) are considerably greater than the size of the cells.

16 Claims, 5 Drawing Sheets

APPARATUS AND METHOD FOR THE CONTINUOUS CULTIVATION OF MICROORGANISMS IN A CULTURE LIQUID

This application is a continuation of application Ser. No. 06/934,110 filed Nov. 24, 1986, now abandoned.

BACKGROUND OF THE INVENTION

Field of the Invention

The invention relates to an apparatus for the continuous cultivation in suspension of microorganisms, and also of animal and vegetable cells, in a culture liquid, which apparatus contains a cultivation tank provided with a stirring device, which tank is provided with an inlet for fresh cultivation medium and an outlet for used culture liquid, which tank contains a rotating separating device for separating suspended cells or cell-carrying particles from the culture liquid passed through the separating device, which separating device is provided with a collecting space for culture liquid rendered essentially free of cells into which the outlet for the culture liquid, rendered essentially free of cells, debouches.

For cultivating cells and other microorganisms in a culture liquid it is known that use is made of the so-called continuous perfusion system. In said system a rotating filter is used in a so-called fermenter or bioreactor, which filter has a pore size which is smaller than the diameter of the microorganisms, or cells or cell-carrying particles in the culture liquid which have to be separated. In this process medium is continuously supplied to the cultivation tank, the so-called fermenter or bioreactor, while culture liquid which is essentially free of cells is removed from the collecting zone located inside the filter. In this manner relatively high concentrations of microorganisms, or cultivated cells can be obtained along with the high product concentrations associated therewith in the culture liquid drained off.

A rotating filter is used inorder to prevent obstruction of the filter surface as far as possible- Centrifugal and shearing forces are exerted on the cell material deposited against the outside of the rotating filter as a result of which said cell material can at least to a large extend be removed from the filter surface. In practice, however, it has emerged that the rotating filters nevertheless become blocked within, in many cases, an undesirably short period, as a result of which limits are imposed on the product yield.

SUMMARY OF THE INVENTION

The object of the invention is to avoid the abovementioned disadvantage of the known systems and according to the invention said object is achieved in that the rotating parts of the separating devices are formed in a manner such that, within the surface of revolution in which the outside circumference of the rotating parts rotates about an axis of rotation, a zone is formed containing a vortex-free vertical rotating column of culture liquid from which the cells which are in suspension ae thrown back by centrifugal forces into the surrounding culture liquid through openings in the outside circumference of the separating device which are considerably larger than the size of the cells to be separated.

The separating device according to the invention with the features listed above differs essentially from the known rotating filters in that only centrifugal forces are used for separating cells or cell-carrying particles, which centrifugal forces are produced in the vortex-free, laminary flowing, axial rotating column of culture liquid, the particles thrown out of said liquid column being thrown back again into the surrounding culture liquid without being held back by the presence of a filter containing pores. This avoids the risk of blockages being produced and consequently of faulty operation and, after a relatively short time has elapsed even of complete obstruction of the separating device.

The separating device to be used can be embodied in various manners.

According to one embodiment, the separating device contains at least one vertical hollow cylindrical drum which is concentrically attached to a rotating shaft, is closed off at the bottom and has a perforated wall, the perforations having a size which is considerably greater than the sizes of the cells or cell-carrying particles to be separated. The diameter of the drum and speed of rotation can be fixed for each application in a manner such that a zone with minimum turbulence is produced within the cylindrical drum. Extraction of culture liquid which is essentially free of cells takes place from the chamber inside the cylinder near the rotating shaft.

A variant is obtained according to the invention in that the cylindrical drum is provided on the inside with fins, uniformly distributed over the circumference, which extend radially inwards and over the full height of the drum. In this case, the fins may extend radially inwards over the same distance over their entire length from the inside wall of the cylinder to a distance from the rotating shaft, or may extend with a lowermost section to the rotating shaft and with an uppermost section to a distance from the rotating shaft. In this case, the extraction of culture liquid takes place from the space between the upper section of the fins and the rotating shaft. In said embodiment a turbulence-free zone is produced in the segments between the fins.

In addition, according to the invention an expedient embodiment is obtained in that the separating device is constructed from two vertical hollow cylindrical drums placed concentrically inside each other with different diameters and which are jointly attached to a central rotating shaft, of which at least the inner drum is closed off at the bottom and which drums are provided with perforations in their walls, the sizes of which are larger than those of the cells or cell-carrying particles to be separated. In this case, the ratio of the diameters of the cylinders can be selected for each system in a manner such that minimum turbulence is produced between the cylinders. Here, the extraction of culture liquid takes place from the space between the innermost cylinder and the rotating shaft.

A further efficiently woring embodiment of the apparatus according to the invention, having at least one vertical cylindrical perforated drum attached to a central rotating shaft, is obtained by surrounding the cylindrical drum, at least the lower part thereof, by a cylinder with a larger diameter, said cylinder having a non-perforated wall and being open at its both ends, said drum and said cylinder being jointly rotatably attached to the rotating shaft and a stirring device being located underneath the drum-cylinder assembly.

Alternatively the perforated cylinder may be partly surrounded by an open ended cylinder with a larger diameter, having a non perforated wall and which is non-rotatably fixed in the cultivated tank, the stirring device being disposed within said cylinder at some distance underneath the bottom of the cylindrical drum, said fixed cylinder being further provided with flow guiding means for providing and forcing an axial laminar flow in resp. through the annular space between said cylinder and said drum.

Said surrounding cylinders have in general the effect of creating such flow conditions in the space between the drum and the cylinder and therefore at the outside of the perforated drum, that the forming of a vortex free axial liquid column within the drum is not or minimally affected by distributing flow effects from the surrounding liquid in the tank.

According to the invention another embodiment can be obtained in that the rotating assembly consists of fins, uniformly distributed over the circumference of, and attached to, the rotating shaft, which extend radially outwards and extend vertically over a distance of the rotating shaft.

In this case, the number and the sizes of the fins can be designed in a manner such that no turbulence is produced between the fins and radial centrifuging of the suspended particles does in fact take place. Here, extraction of the culture liquid, which is essentially free of cells, can take place from a space at the inside of the fins which is formed by a recess provided in the top of the fins.

Yet another embodiment is obtained in that the separating device is constructed from a number of rotating dish-shaped elements situated at an angle to the rotating shaft and mounted at a distance of one millimeter at the most from each other. In this case, the culture liquid enters between the dishes from the outside and can centrally pumped away at the top in the vicinity of the rotating shaft in a recess provided at that point. However, according to a preferred embodiment of this construction the sized cultivation liquid, which has been rendred free or substantial free of cells, can be centrally pumped away through an opening in the rotating shaft, which is at least partly made hollow and is connected to an outlet tube, preferably at the bottom of the shaft, passing through the bottom of the tank.

The rotating assemblies may be attached to the rotating shaft of the stirring element or attached to a separate rotating shaft which extends into the cultivation tank.

The last-named possible embodiment has the advantage that the rotation speed of the separating element can be regulated and adjusted independently of the rotation speed of the stirring element.

BRIEF DESCRIPTION OF DRAWINGS

The invention will now be explained in more detail on the basis of the drawing in which some embodiments of the equipment according to the invention are shown by way of example.

FIGS. 3 and 3a show respectively a vertical section through a bioreactor and a plan view of the separator used therein which is a variation of the separator shown in FIGS. 2 and 2a.

FIGS. 7 and 7a show respectively a variant of the bioreactor of FIGS. 6 and 6a.

DETAILED DESCRIPTION

Figure 1:
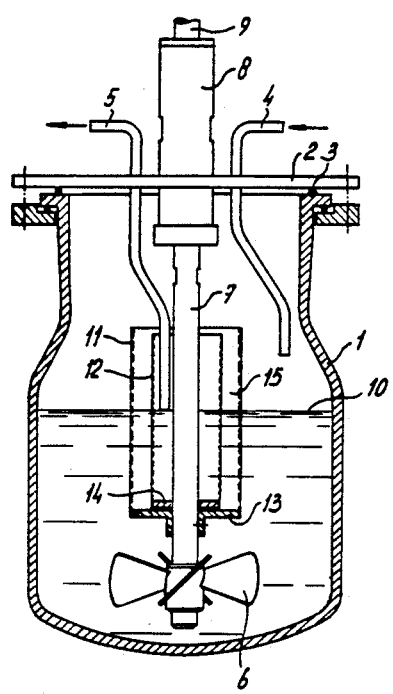
FIG. 1 shows a vertical section through a bioreactor according to the invention in which the separator is constructed from two cylinders concentrically placed inside each other.

In the figures, corresponding components are indicated by the same reference numerals.

In each of FIGS. 1, 2, 3, 4 and 5 a bioreactor is shown which consists of a tank 1 which is sealed at the top by a cover 2 which is in contact with the top opening of the tank 1 via a sealing ring 3 to produce a seal. Through the cover there is passed, on the one hand, and inlet pipe 4 for supplying culture medium for cultivating, for example animal cells in the tank, and on the other hand, an outlet pipe 5 for removing used culture liquid, which is essentially free of cells, from the respective separator to be described in more detail below. In addition, there is provided in the tank 1 a stirring device which consists of a stirring element 6 which is attached to a vertical rotating shaft 7 which is linked to the outgoing shaft 9 of a drive motor (not shown) via a connecting bush 8 passed in a seal-forming manner through the cover 2. In the figures shown a section of the tank 1 is filled with cultivating medium 10 to which the cell material to be cultivated is supplied. During operation the liquid 10 is intensively mixed by the stirring element 6 in the tank to obtain a good mixing between the cultivating medium and culture in order to obtain a homogeneous suspension of the cells in the medium.

A separating device with centrifugal action is provided in each of the bioreactors shown in FIGS. 1 to 5 incl., the outlet pipe 5 debouching in all the embodiments inside the separating device while the inlet pipe debouches outside the separating device at the top of the tank 1. With constant supply and constant removal of medium, this produces a flow of medium from the tank to the inside of the separating device. In FIG. 1 the separating device consists of two concentric cylindrical drums 11 and 12 which are permanently attached to the rotating shaft 7 of the stirring element 6. Both drums have a perforated wall, the perforations being considerably greater than the particles (cells or cell-carrying particles) suspended in the medium 10. They consist, for example, of pores made of stainless steel. The drums are closed at the bottom, the bases 13 and 14 respectively of the drums being mounted on the shaft in a seal-forming manner.

The outlet pipe 5 debouches in the vicinity of the shaft 7 inside the innermost cylindrical drum 12.

The ratio of the diameters of the drums 11 and 12 may be chosen in a manner such that, with a given rotary speed of the rotating shaft of the stirrer and a given medium in the tank 1, a vortex-free column of liquid is formed which rotates along with the cylinders in the annular space 15 between the cylinders 11 and 12, in which column of liquid the cells or cell-carrying particles suspended therin are subjected to the centrifugal force generated therein and as a consequence are thrown back through the large pores in the wall of the cylinder 11 into the medium 10 situated in the tank. As a result of the continuous supply and removal of medium a continuous perfusion system is obtained which is not obstructed by the occurrence of filter material blockages.

Figure 2:
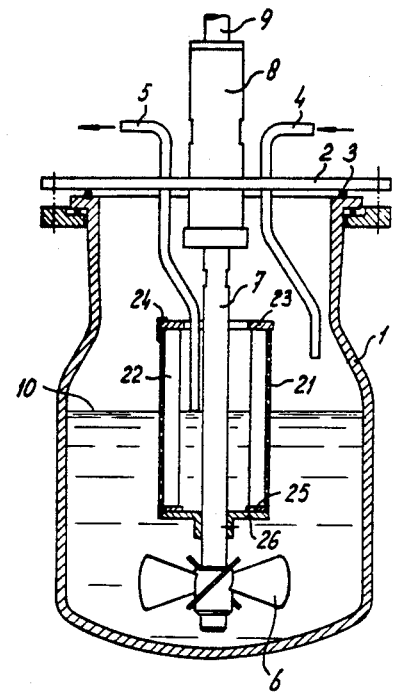
FIGS. 2 and 2a show respectively a vertical section through a bioreactor and a plan view of the separator used therein which comprises a rotating cylinder provided with fins on the inside.
Figure 1A:
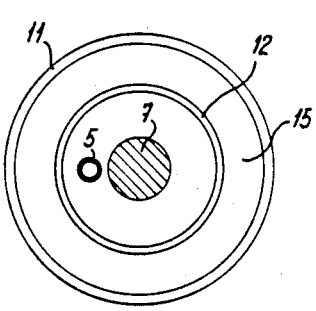
Figure 2A:
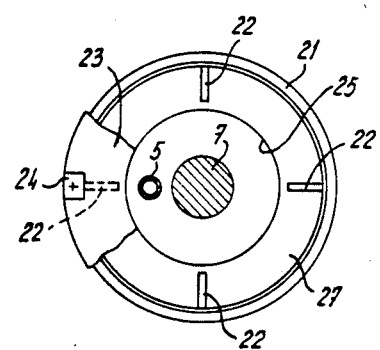

In the embodiment shown in FIGS. 2 and 2a use is made of a cylindrical drum 21 with relatively large perforations in the wall thereof, which drum is closed at the bottom by a base 26 attached to the rotating shaft of the stirrer. On the inside of the drum there are provided fins 22 which extend radially inwards and the tops of which are attached to a ring 23 mounted on the upper wall of the drum 21 at 24 and a bottom of which is attached to a ring 25 which fits within the drum and rests on the base 26 thereof. The outlet pipe 5 is passed at the top through the ring 23 into the space between the fins 22 and the rotating shaft 7. In the embodiment in FIGS. 3 and 3a there are provided fins 32 extending radially inwards inside the cylindrical drum 31 which has relatively large perforations in the wall and corresponds to the drum 21 in FIG. 2, of which fins the lower section extend to the rotating shaft 7 and the upper sections contain a recess 34 into which the outlet pipe 5 debouches. In said embodiment the lower sections of the fins are attached to a bush 33 which is firmly attached to the rotating shaft 7.

Figure 3:
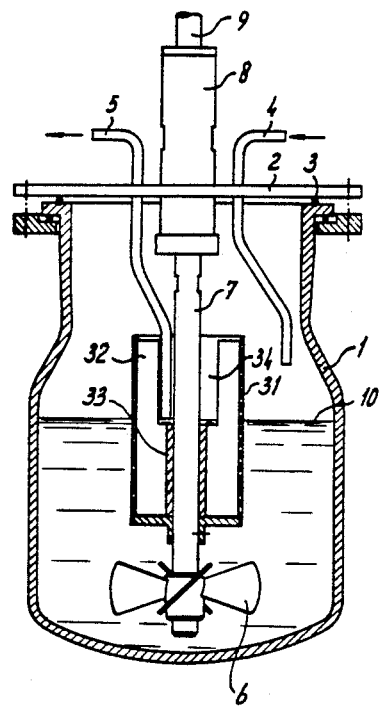
Figure 3A:
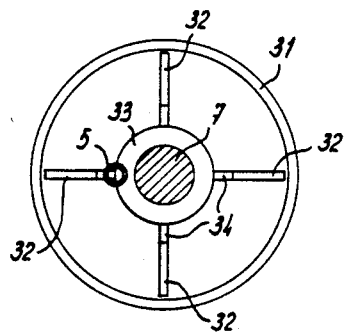

In the embodiment in FIGS. 2 and 3 the rotating drum 21 or 31 respectively is partially or wholly divided on the inside into segments, in which segments, if the choice of number and sizes of the fins is correct, a column of liquid is produced which is virtually free of vortices and rotates.

The material of the fins must, of course, be compatible with the medium of which it is used and consist preferably of stainless steel, as do the drums used.

Figure 6:
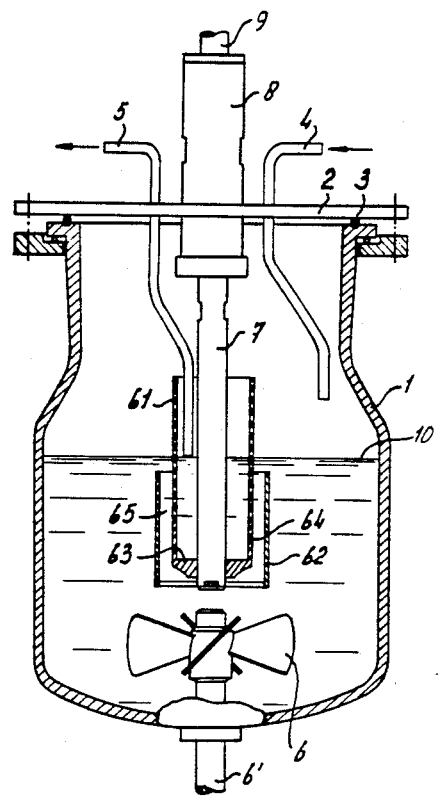
FIGS. 6 and 6a show respectively a vertical section through a bioreactor and a plan view of the separator used therein, comprising a perforated drum of which the lower part is surrounded by a non perforated cylinder.

FIG. 6 shown an embodiment of a separator comprising a perforated drum 61 of which the size of the perforations are considerably greater than the particles suspended in the medium 10. The drum 61 is sealingly attached to the rotating shaft 7 by means of its closed bottom 63. The lower part of drum 61 is concentrically surrounded by a cylindrical member 62 having a non perforated wall and which is open ended. Said cylindrical member is also attached to the rotating shaft through attachments known per se. A stirring device 6 is provided at some distance undeneath the cylinder-drum assembly and is separately driven by a motor (not shown) through the shaft 6' passing sealingly through the bottom of the tank 1.

With a proper selection of diameter, position and shape, of the cylindrical member 62, which shape could be cylindrical and/or conical, a small vertical flow will be created in the rotating liquid column in the space 65 between the drum and the cylinder 62, by which cells, which are thrown out from the vortex free vertical rotating liquid column formed within the drum 61 by centrifugal action, will be entrained and carried to the surrounding cultivation liquid 10.

This prevents the thrown out cells from reentering the vortex-free vertical rotating liquid columns formed within the drum 61 under the influence of flow conditions in the surrounding cultivations liquid 10. This effect of preventing reentering of thrown out cells in the perforated drum is supported by making the lowermost part 64 of the drum 61 non-perforated.

Figure 7:
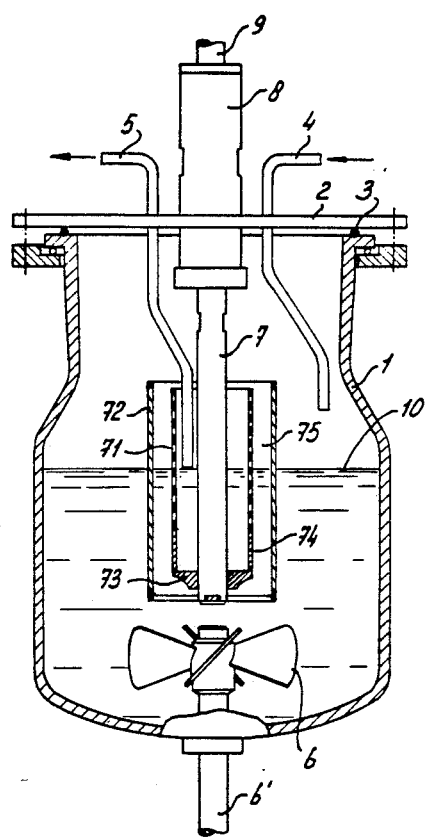
Figure 6A:
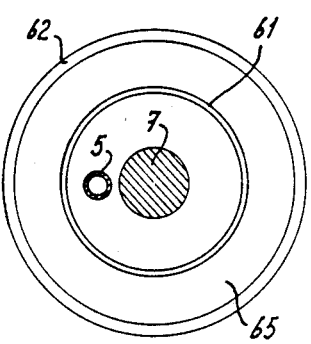
Figure 7A:
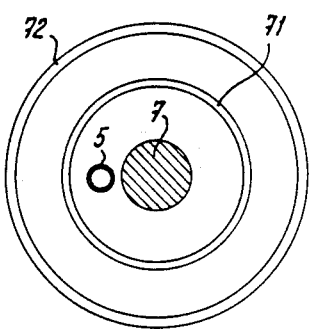

FIG. 7 shows a variant of the separator according to FIG. 6. According to this variant a rotating cylindrical, perforated drum 71 with a closed bottom 73 is completely surrounded by a non-perforated open-ended cylindrical member 72, herein the cylinder-drum assembly projects above the liquid level in the tank. With a proper selection of diameter and shape, a vortex-free, rotating column is created within the drum 72 as well as in the space 75 between the drum 71 and the cylindrical member 72 from which the cells are thrown by centrifugal action against the inner wall of the cylindrical member 72, which cells by gravity action progressively move downwardly along said wall into the surrounding liquid 10. In this way the vortex-free vertical column which is formed in the drum 71 is protected against disturbing effects of the flow conditions in the surrounding liquid 10. The lower part 74 of the perforated drum 71 is made non-perforated to prevent cells from reentering directly the drum 71.

Figure 8:
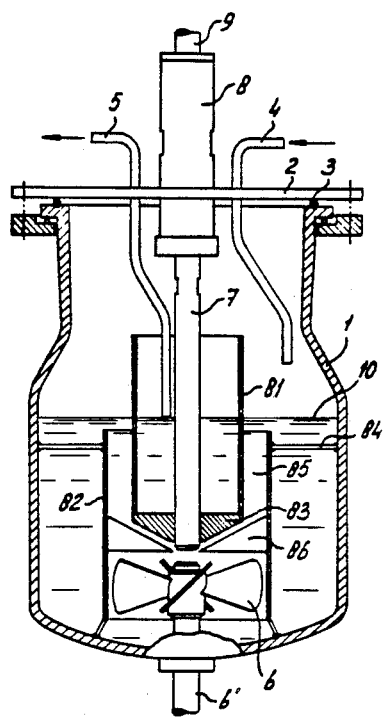
FIGS. 8 and 8a show a bioreactor of the invention comprising a perforated drum of which the lower part is surrounded by a fixed non-perforated cylinder.

In the embodiment according to FIG. 8 a perforated cylindrical drum 81, which is attached to the rotating shaft 7 by means of its closed bottom 83, is partly surrounded by a non perforated open-ended cylindrical member 82 which is non-rotatably attached to the inner wall of tank 1 by attachment members 84. The lower part of the cylindrical member 82 extends beyond the bottom of the perforated drum 81. A separately driven stirring device 6 is located within the lower part of the cylindrical member 82 and guiding means 86 are attached to the inner wall of the cylindrical member 82.

In the arrangement of separator turbulent flows which are created by the stirring device 6 are substantially transferred to a vertical lammar flow by the guiding means 86 which flow is forced through the space 85 between the perforated drum 81 and the cylindrical member 82. In this way favourable flow conditions are created along the outside of drum 82 so that the vortex free vertical liquid column formed within the drum 81 will not be affected by disturbing flow effects at the outside of the drum.

Figure 5:
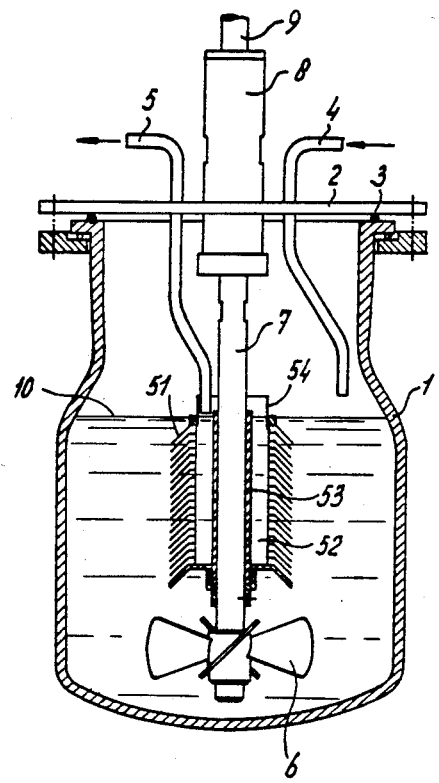
FIGS. 5 and 5a show respectively a vertical section through a bioreactor and a plan view of the separator used therein, which contains rotating concentric dishes situated at an angle to the shaft.
Figure 5A:
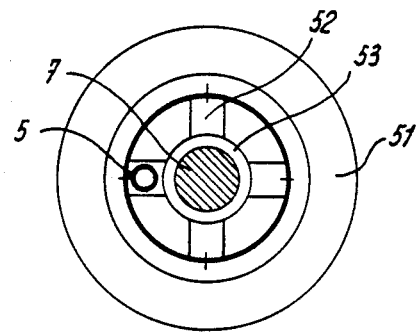

FIG. 5 shows an embodiment of a separator, the rotating assembly of which is formed from a number of dish-shaped elements 51 which are attached in a rotationally fixed manner to the rotating shaft 7 at a distance of one millimeter at the most from each other and at an angle to the rotating shaft. The dish-shaped elements are attached to radial arms 52 which project radially from a bush 53 which is permanently attached to the rotating shaft 7.

At the top the assembly is provided with a cylindrical ring 54 inside which the outlet pipe 5 debouches in order to remove medium which flows out between the dishes 51 to the inside from the surrounding space in the tank 1. Between the dishes the liquid is in a virtually turbulence-free rotating state, the particles which are in it being thrown back by centrifugal force into the surrounding medium in the tank 1.

Figure 9:
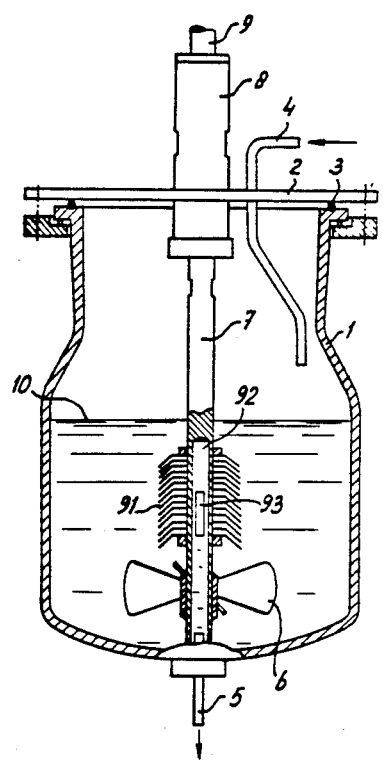
FIGS. 9 and 9a show a variant of the bioreactor according to FIG. 5.
Figure 8A:
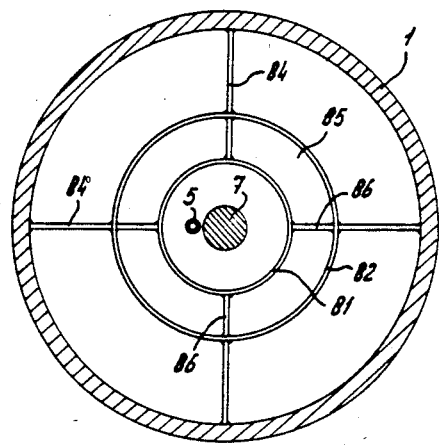
Figure 9A:
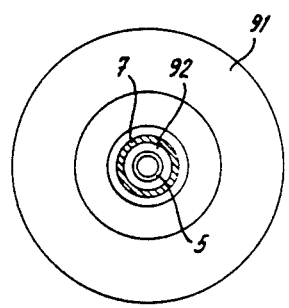

FIG. 9 shows a variant of the embodiment according to FIG. 5. Contrary to the construction according to FIG. 5 the dish-shaped elements are in the form of a packet directly attached to the rotating shaft 7 which rotating shaft 7 is rotably beared in bearings in cover 2 of the tank 1 as well as in the bottom of the tank 1. The rotating shaft has inwardly a hollow portion 92 and which hollow portion communicates with the central spacings between the dish-shaped elements 91 through an opening 93. A liquid outlet 5' is debouching in the lower end of the hollow portion 92 of the shaft 7. The stirring device 6 is attached to the rotating shaft 7.

With this arrangement the liquid which is rendered free from cells is removed through the hollow portion 92 and outlet 5' at the bottom of the tank 1.

With respect ot the embodiment according to FIG. 5 this construction has following advantages:
- because the outlet pipe 5' is not projecting in the collecting chamber 93 for liquid which is made free from cells, a vortex free zone is also created in the collecting chamber
- because of the double bearing of the rotating shaft 7, the shaft is stabilized, also at high rotation speeds. This is very desirable to prevent turbulencies around the packet of dish-shaped elements
- the packet can be completely immersed in the liquid, so that the liquid level is no longer of importance
- There is no risk that the separator will be emptied at high rotation speed, because there will be an over pressure in the bioreactor with respect to the collecting chamber in the hollow shaft when the separator is completely immersed.

Figure 4:
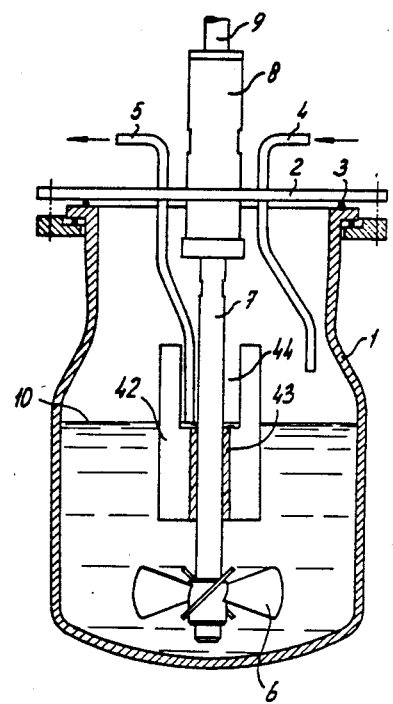
FIGS. 4 and 4a show respectively a vertical section through a bioreactor and a plan view of the separator used therein, which separator consists of rotating vertical fins mounted on the rotating shaft.
Figure 4A:
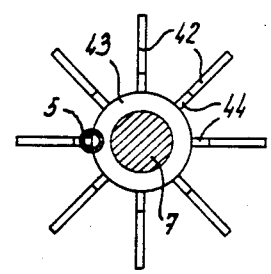

In the embodiment shown in FIGS. 4 and 4a the separator is formed from vertical fins 42 which extend radially at distances which are equal to each other and are attached to the rotating shaft 7 by means of a bush 43 mounted on the rotating shaft. The fins are provided at the top with a recess 44 into which the outlet pipe 5 debouches. The fins 42 are embodied in a number and with sizes such that no turbulence, or virtually no turbulence, is produced between the fins and radial centrifuging of the suspended particles does in fact take place.

The advantages of the invention will now be demonstrated on the basis of the results of a test carried out by the Applicant with a bioreactor designed according to FIG. 1 compared with the results of a bioreactor embodied with a rotating filter having a pore size smaller than the size of the cells.

On the one hand, a cultivation was carried out using hybridoma cells in a continuous 3-liter perfusion culture, a bioreactor being used which contained a rotating cylindrical filter with a pore size of 10 μm, while on the other hand, the same cultivation was carried out with a bioreactor in which use was made of a rotating continuous separator having two concentric cylinderical "sieves" according to FIG. 1. The sieves had a ratio of diameters of approximately 3:4 and a pore size of about 75 μm, which is approximately 7 times the size of the hybridoma cells. The results of the tests carried out are shown in Tables I and II below.

TABLE I

Cultivation of hybridoma cells in a 3-liter continuous perfusion culture by means of a sieve having a pore size of 10 μm

| Culti- | Cells/ml × $10^3$ | | | | |
|---|---|---|---|---|---|
| vation | Culture | | Harvest | | |
| days | living | dead | living | dead | Notes |
| 0 | 245 | 6 | | | |
| 1 | 320 | 8 | | | |
| 2 | 510 | 43 | — | — | start of perfusion |
| 3 | ± 700 | 192 | | | |
| 4 | 900 | 140 | 15 | 18 | |
| 5 | 1150 | 152 | 20 | 13 | |
| 6 | 1526 | 200 | 21 | 17 | |
| 7 | 2800 | 375 | 38 | 30 | |
| 8 | 4400 | 550 | 131 | 77 | |
| 9 | 2850 | 450 | 90 | 130 | |
| 10 | 3500 | 500 | 350 | 250 | |
| 11 | 3900 | 900 | 240 | 172 | |
| 12 | 3500 | 800 | 178 | 178 | |
| 13 | 5600 | 1288 | 1068* | 366 | obstruction of 10 μm sieve |

*high cell concentration harvest due to sieve running over

TABLE II

Cultivation of hybridoma cells in a 3-liter continuous perfusion culture by means of a centrifugal separator with two concentric cylinders both having a pore size of about 75 μm

| Culti- | Cells/ml × $10^3$ | | | | |
|---|---|---|---|---|---|
| vation | Culture | | Harvest | | |
| days | living | dead | living | dead | Notes |
| 0 | 260 | 18 | — | — | start of perfusion after 2 days, 3 l/day |
| 5 | 1660 | 600 | 50 | 82 | |
| 10 | 1825 | 654 | 550 | 340 | |
| 15 | 6300 | 3450 | 250 | 425 | |
| 20 | 7150 | 6300 | 175 | 800 | |
| 25 | 7280 | 4220 | 12 | 820 | perfusion increased from 3 to 5 l/day after 24 days |
| 30 | 9450 | 5350 | 790 | 1240 | |
| 35 | 10200 | 4450 | 670 | 785 | perfusion decreased from 5 to 3 l/day after 27 days |
| 40 | 6200 | 8000 | 630 | 2820 | perfusion decreased from 3 to 1.5 l/day after 40 days |
| 45 | 5420 | 6760 | 405 | 3200 | |

From the tables it emerges that after about 13 cultivation days the filter with a pore size of 10 μm used in the bioreactor was obstructed and the cultivation process had to be stopped, while the bioreactor using "centrifugal separator" according to FIG. 1 still continued to be effective after 45 cultivation days, much higher culture yields also being obtained.

It is pointed out that the invention is not limited to the exemplary embodiments show and discussed herein but also extends to modified embodiments which fall within the scope of the invention as described in the claims. Thus, the separating device in the bioreactor may contain only one cylindrical drum attached to a rotating shaft in the bioreactor, the wall of which drum is provided with pores the sizes of which are larger than those of the cells or cell-carrying particles to be separated. Further the bottom 13 of the outer drum 11 of the embodiment according to FIG. 1 could be perforated, in stead of closed such as shown in FIG. 1. It is without saying that where the stirring device 6 in FIGS. 1–5 are shown as to be driven by the rotating shaft 7 of the separator assembly, it could be arranged in the way as shown in FIGS. 6, 7 and 8, i.e. separated from the rotating shaft 7 and separately driven by a separate drive shaft.

Further it should be understood that the term stirring device as used herein is meant to include all devices creating a circular and mixing movement in the liquid and should not be understood as to be limited to the stirring devices as shown in the drawings.

We claim:

1. Apparatus for the continuous cultivation of cells of a predetermined size of organisms selected from the group consisting of micro-organisms, and animal and vegetable cells, in a culture liquid, which apparatus contains a cultivation tank provided with a stirring device, an inlet for fresh cultivation medium, an outlet for used culture liquid, a rotating separating device comprising rotating parts for separating suspended cells or cell-carrying particles from culture liquid passed through the separating device which separating device is provided with a collecting space for culture liquid rendered essentially free of said cells into which the outlet for the culture liquid, rendered free of the cells, debouches, characterized in that the rotating parts of the separating device are formed in a manner such that, within the surface of revolution in which the outside circumference of the rotating parts rotates about an axis of rotation, a zone is formed containing a vortex-free axial rotating column of culture liquid from which the cells which are in suspension are thrown back by centrifugal forces into the surrounding culture liquid through openings in the outside circumference of the separating device which are considerably larger than the size of the cells to be separated, said openings being considerably larger than said predetermined cell size.

2. Apparatus according to claim 1 characterized in that the separating device contains at least one vertical cylindrical drum which is attached to a central rotating shaft, is closed off at the bottom and has a perforated wall, the perforations having a size which is considerably greater than the sizes of the cells or cell-carrying particles to be separated.

3. Apparatus according to claim 2, characterized in that the cylindrical drum is provided on the inside with fins, uniformly distributed over the circumference, which extend radially inwards and over the full height of the drum.

4. Apparatus according to claim 3, characterized in that the fins extend inwards with at least a lower part of each fin attached to the central rotating shaft.

5. Apparatus according to claim 2, characterized in that the separating device is constructed from two vertical hollow cylindrical drums placed concentrically inside each other with different diameters and which are jointly attached to a central rotating shaft, of which at least the inner drum is closed off at the bottom and which drums are provided with perforations in their walls, the sizes of which are larger than those of the cells or cell-carrying particles to be separated.

6. Apparatus according to claim 2, characterized in that the cylindrical drum at least about its lower part is concentrically surrounded by a cylinder with a larger diameter, said cylinder having a non-perforated wall and being open at both ends, said drum and said cylinder being jointly rotatably attached to the rotating shaft, a stirring device being located underneath the cylinder-drum assembly.

7. Apparatus according to claim 6, characterized in that said non-perforated cylinder surrounds said drum over the whole height thereof.

8. Apparatus according to claim 6, characterized in that the vertical wall of the inner drum is non-perforated at its lower part adjacent the closed bottom of the drum.

9. Apparatus according to claim 8, characterized in that the separate rotation shaft is driven by a separate drive device.

10. Apparatus according to claim 8, characterized in that the rotating shaft of the separating device is driven through a transmission mechanism by the rotating shaft of the stirring device.

11. Apparatus according to claim 2, characterized in that the cylindrical drum is partly surrounded by an open ended cylinder with a larger diameter, having a non-perforated wall and which is non-rotatably fixed in the cultivation tank, the stirring device being disposed within said cylinder at some distance underneath the bottom of the cylindrical drum, said fixed cylinder being further provided with flow guiding means for providing and forcing a vertical laminar flow in the annular space between said cylinder and said drum.

12. Apparatus according to claim 1, characterized in that the rotating assembly is provided on the rotating shaft of the stirring element.

13. Apparatus according to claim 1, characterized in that the rotating assembly is provided on a rotating shaft in the cultivation tank separate from the stirring element.

14. Apparatus according to claim 1, characterized in that the rotating assembly consists of fins, uniformly distributed over the circumference of, and attached to, the rotating shaft, which extend radially outwards and extend vertically over a distance of the rotating shaft.

15. Apparatus according to claim 1, characterized in that the separating device is constructed from a number of rotating dish-shaped elements situated at an angle to the rotating shaft and mounted at a distance of one millimeter at most from each other.

16. Method for cultivating organisms selected from the group consisting of animal and vegetable cells and micro-organisms comprising the step of choosing cells for culture having a predetermined size and subjecting the cells to continuous cultivation in suspension in a culture liquid in a cultivation tank, said tank being provided with a stirring device, an inlet for continuously supplying fresh cultivation medium, an outlet for used culture liquid, a rotating separating device comprising rotating parts for separating suspended cells or cell-carrying particles from culture liquid being passed through the separating device, culture liquid rendered essentially free of cells being collected in a collecting space of the separating device and being withdrawn continuously from said space through an outlet debouching into it, the method further comprising the step of continuously supplying the culture liquid containing cells to the separating device, causing the liquid to revolve in a manner that, within the surface of revolution in which the outside circumference of the rotating liquid rotates about an axis of rotation, a zone is formed containing a vortex-free axial rotating column of culture liquid from which the cells, which are in suspension are thrown back by centrifugal forces into the surrounding culture liquid through openings in the outside circumference of the separating device, the said openings being considerably larger than said predetermined cell size.

* * * * *